United States Patent
Rutenberg

(10) Patent No.: US 8,846,338 B2
(45) Date of Patent: *Sep. 30, 2014

(54) PROCESSES FOR THE PREPARATION OF PHOSPHATIDES

(75) Inventor: David Rutenberg, Haifa (IL)

(73) Assignee: Lipogen Ltd., Haifa (IL)

( * ) Notice: Subject to any disclaimer, the term of this patent is extended or adjusted under 35 U.S.C. 154(b) by 1097 days.

This patent is subject to a terminal disclaimer.

(21) Appl. No.: 12/502,258

(22) Filed: Jul. 14, 2009

(65) Prior Publication Data

US 2010/0036141 A1 Feb. 11, 2010

(30) Foreign Application Priority Data

Aug. 7, 2008 (IL) .......................................... 193303

(51) Int. Cl.
*C12P 1/00* (2006.01)
*C12P 13/06* (2006.01)
*C12P 7/64* (2006.01)
*C12P 9/00* (2006.01)

(52) U.S. Cl.
CPC ............... *C12P 7/6481* (2013.01); *C12P 13/06* (2013.01); *C12P 9/00* (2013.01)
USPC ............................................ 435/41; 554/79

(58) Field of Classification Search
CPC .................................................... C12P 7/6481
See application file for complete search history.

(56) References Cited

U.S. PATENT DOCUMENTS

| | | | | |
|---|---|---|---|---|
| 5,188,951 | A * | 2/1993 | Tremblay et al. | 435/131 |
| 6,410,522 | B1 * | 6/2002 | Ruenberg | 514/114 |
| 6,492,146 | B1 | 12/2002 | De Ferra et al. | |
| 6,706,280 | B2 * | 3/2004 | Tournier et al. | 424/450 |
| 2002/0072508 | A1 | 6/2002 | Rutenberg | |

FOREIGN PATENT DOCUMENTS

| | | |
|---|---|---|
| EP | 0 776 976 A2 | 6/1997 |
| EP | 1223222 A1 | 7/2002 |
| WO | WO 00/56869 A2 | 9/2000 |
| WO | WO 00/77183 B1 | 12/2000 |
| WO | WO 02/090560 A2 | 11/2002 |

OTHER PUBLICATIONS

Rewald, B., phosphatides form oil seeds, 1942, Biochem. J., 36, pp. 822-824.*
Hellhammer, J., et al., Effects of soy lecithin phosphatidic acid and phosphatidylserine complex (PAS) on the endocrine and psychological resposes to mental stress, 2004, 7 (2), pp. 119-126.*
Extended European Search Report in parallel prosecution of patent application No. EP 09166900.2, Ad (Berlin), dated: Jan. 4, 2011.
European Official Action in parallel prosecution of patent application No. EP 09166900.2, Ad, dated Sep. 21, 2011.
H. Mori, et al, Amino-Acid-Based Block Copolymers by RAFT Polymerization, Macromolecular Rapid Communications, 2012, 33, 1090-1107, www.mrc-journal.de.
I. Fuchs, et al, Induction of Amphiphilicity in Polymer@Silica Particles: Ceramic Surfactants, Langmuir, 2013, 29, 2835-2842, pubs.acs.org/Langmuir.

* cited by examiner

*Primary Examiner* — Yate K Cutliff
(74) *Attorney, Agent, or Firm* — Reuven K. Mouallem, Esq.; FlashPoint IP Ltd.

(57) ABSTRACT

The present invention discloses processes for the preparation of phosphatides and salts thereof, the processes including the steps of: using at least one raw material lecithin as a substrate and a water-insoluble surfactant-matrix material having a particulate size greater than about 0.01 mm; and enzymatically processing at least one raw material lecithin with the water-insoluble surfactant-matrix material, phospholipase-D, racemic or enantiomerically-pure serine, amino acid, and/or amine and salts in a pH-buffered aqueous solution, wherein the step of processing is performed in a single-phase reaction environment, to produce phosphatides, or the salts thereof, having a structural fatty-acid chain derived from at least one raw material lecithin. Preferably, the step of processing is performed in the presence of a buffer having a pH in the range of about 4.5-8.0. Preferably, the step of processing is performed in the presence of a calcium salt.

18 Claims, No Drawings

PROCESSES FOR THE PREPARATION OF PHOSPHATIDES

This patent application claims priority under 35 U.S.C. §119(a) to Israeli Patent Application No. 193303, filed Aug. 7, 2008, which is hereby incorporated by reference in its entirety.

FIELD AND BACKGROUND OF THE INVENTION

The present invention relates to processes for the preparation of phosphatides and salts thereof in general. In particular, the present invention relates to processes for the preparation of specific phospholipids starting from standard natural phospholipids that are reacted in the presence of a water-insoluble stationary surfactant-matrix material.

Specific phospholipids such as phosphatidylserine, phosphatidic acid, and some phosphatidylglycerols are used in pharmaceutical compositions, nutritional compounds, and functional foods.

The importance of phosphatidylserine as a functional ingredient was demonstrated in 2003 when the US FDA allowed two qualified health claims in which the usage of phosphatidylserine was related to the reduction of cognitive-dysfunction risk and dementia in the elderly.

In the prior art, Hellhammer et al. ("Effects of Soy Lecithine Phosphatidic Acid and Phosphatidylserine Complex (PAS) on the Endocrine and Psychological Responses to Mental Stress," Stress, The International Journal on the Biology of Stress, Vol. 7, No. 2, 119-126, June, 2004) reported that the oral administration of phosphatidic acid and phosphatidylserine complex resulted in a dampening effect of the pituitary adrenal reactivity (ACTH, cortisol) and the psychological response (Spielberger's State-Trait Anxiety Inventory (STAI) stress subscale) to mental and emotional stress. The results indicated that the oral administration of phosphatidic acid and phosphatidylserine complex can be used as a treatment of stress-related disorders.

Eibl et al describe the "Preparation of phospholipids analogs by phospholipase-D" ("Methods in Enzymology," Vol. 72, pages: 632-639, 1981).

De Ferra et al., in U.S. Pat. No. 6,492,146 (hereinafter De Ferra '146), disclose a process for the preparation of phosphatidylserine with racemic or enantiomerically pure serine (i.e. (L)-serine) in the presence of the enzyme phospholipase-D (PLD) and a surfactant in a quantity not greater than 0.4 grams per gram of substrate in which the reaction medium is an aqueous dispersion free of organic solvents. According to De Ferra '146, the main advantage of the process is the possibility to carry out the transphosphatidylation reaction of phosphatidylcholine, and of similar phosphatides in an aqueous medium, to obtain phosphatidylserine of good purity with highly-satisfactory yields and with minimal phosphatidic acid by-product.

Typically, a solvent is used to completely dissolve the lecithin in such reactions. A dissolved solution, as opposed to a suspension, makes the process easier to manage.

Basheer, in WO Patent Publication No. 2000/056869 (hereinafter Basheer '869), discloses a process of preparing for inter- and/or trans-esterification of oils and fats in hydrophobic organic media using an insoluble matrix-immobilized surfactant-coated-lipase complex as a biocatalyst. The preparation of the insoluble matrix-immobilized surfactant-coated lipase complex includes, in any desired order, the steps of: contacting a lipase with a surfactant, and contacting the lipase with an insoluble matrix at a concentration to obtain immobilization of the lipase on the matrix.

Basheer et al., in WO Patent Publication No. 2002/090560 (hereinafter Basheer '560), disclose an enzyme-catalyzed synthetic process for the production of glycerophospholipids and their synthetic or natural analogues. The process provides an enzymatic esterification/transesterification (acylation) process for the production of 1,2-diacylated and 1-acylated-2-lysophospholipids using glycerophosphorylcholine (GPC) as a substrate or analogue derivatives in which the choline moiety can be substituted by ethanolamine, serine, inositol, glycerol, or any other alcohol, together with a fatty-acid derivative. The reaction can be performed in a solvent, or in a solvent-water system in which a microaqueous sub-system is generated, and in the presence of a phospholipase which may be non-immobilized and surfactant-coated, or preferably, immobilized onto an insoluble matrix, and optionally surfactant-coated (modified). The process leads to the formation of 1-acyl-2-lyso-glycerophospholipids and 1,2-di-acylated glycerophospholipids with a high conversion rate.

Rutenberg, in U.S. Pat. No. 6,410,522 (assigned to the assignee of the present invention and hereby incorporated by reference as if fully set forth herein), teaches an anti-depressant, stress suppressor, and mood improver having a prominent action for decreasing blood cortisol level and serotonin reuptake, and has an effect of alleviating symptoms associated with depression and mental & emotional stress of a subject administered with the improver.

It would be desirable to have processes for the preparation of phosphatides and salts thereof in which the reaction is carried out in a non-solvent, aqueous medium in the presence of a water-insoluble stationary surfactant-matrix material acting as a catalyst in which the process enables the production and separation of phosphatides with no need for further costly extraction of surfactant material from the reaction mixture with solvents.

SUMMARY OF THE INVENTION

It is the purpose of the present invention to provide processes for the preparation of phosphatides and salts thereof.

Embodiments of the present invention provide a process in which phosphatidic acid and phosphatidyserine are produced from lecithin by enzymatic conversion in a pH-buffered aqueous solution, racemic or enantiomerically-pure serine, preferably with (L)-serine and salt utilizing phospholipase-D. The reaction is carried out in the presence of a water-insoluble organic, or inorganic, stationary surfactant-matrix material acting as a catalyst. The use of free enzyme provides better access to the substrate. Such a reaction process results in an improvement in the efficiency of the enzyme to catalyze the reaction when compared to a reaction which is not carried out in the presence of the water-insoluble surfactant-matrix material.

Embodiments of the present invention further provide a process for the simultaneous preparation of phosphatidic acid and phosphatidylserine in low-cost industrial scale as an ingredient for dietetic and functional food applications, as well as a process which is safe and may not need further costly extraction of surfactants from the reaction mixture.

Therefore, according to the present invention, there is provided for the first time a process for the preparation of phosphatides, or the salts thereof the process including the steps of: (a) using at least one raw material lecithin as a substrate and a water-insoluble surfactant-matrix material having a particulate size greater than about 0.01 mm; and (b) enzymatically processing at least one raw material lecithin with the water-insoluble surfactant-matrix material, phospholipase-D, racemic or enantiomerically-pure serine, amino acid, and/or amine and salts in a pH-buffered aqueous solution, wherein the step of processing is performed in a single-phase reaction environment, to produce phosphatides, or the salts thereof, having a structural fatty-acid chain derived from at least one raw material lecithin.

Preferably: (i) at least one raw material lecithin is selected from the group consisting of: a vegetal lecithin and a non-vegetal lecithin; (ii) the vegetal lecithin is selected from the group consisting of: soybean lecithin, sunflower lecithin, and rapeseed lecithin; (iii) the non-vegetal lecithin is selected from the group consisting of: milk phospholipids, egg yolk lecithin, and fish lecithin; (iv) the water-insoluble surfactant-matrix material is selected from the group consisting of: a water-insoluble organic surfactant-matrix material and a water-insoluble inorganic surfactant-matrix material; and (v) the phospholipase-D is selected from the group consisting of: vegetal phospholipase-D, bacterial-originated enzyme phospholipase-D, a combination of vegetal phospholipase-D and bacterial-originated enzyme phospholipase-D.

Preferably, the step of processing is performed in the presence of a buffer having a pH in the range of about 4.5-8.0.

Most preferably, the buffer includes a carboxylic acid with a chain length of C2-C8 having a final concentration in the range of 0.01M to 0.3M in the pH-buffered aqueous solution.

Preferably, the step of processing is performed in the presence of a calcium salt.

Preferably, the step of processing is performed at a temperature in the range of about 25-60° C.

Preferably, the phospholipase-D is bound to the water-insoluble surfactant-matrix material or free in the pH-buffered aqueous solution.

According to the present invention, there is provided for the first time a phosphatide, or salt thereof, produced according to the process above.

According to the present invention, there is provided for the first time a process for the simultaneous preparation of a complex of phosphatides including phosphatidic acid and phosphatidylserine, or the salts thereof, the process including the steps of: (a) using at least one raw material lecithin as a substrate and a water-insoluble surfactant-matrix material having a particulate size greater than about 0.01 mm; and (b) enzymatically processing at least one raw material lecithin with the water-insoluble surfactant-matrix material phospholipase-D, racemic or enantiomerically-pure serine, amino acid, and/or amine and salts in a pH-buffered aqueous solution, wherein the step of processing is performed in a single-phase reaction environment, to produce the complex of phosphatides including phosphatidic acid and phosphatidylserine, or the salts thereof, having, having a structural fatty-acid chain derived from at least one raw material lecithin.

Preferably: (i) at least one raw material lecithin is selected from the group consisting of: a vegetal lecithin and a non-vegetal lecithin; (ii) the vegetal lecithin is selected from the group consisting of: soybean lecithin, sunflower lecithin, and rapeseed lecithin; (iii) the non-vegetal lecithin is selected from the group consisting of: milk phospholipids, egg yolk lecithin, and fish lecithin; (iv) the water-insoluble surfactant-matrix material is selected from the group consisting of: a water-insoluble organic surfactant-matrix material and a water-insoluble inorganic surfactant-matrix material; and (v) the phospholipase-D is selected from the group consisting of: vegetal phospholipase-D, bacterial-originated enzyme phospholipase-D, a combination of vegetal phospholipase-D and bacterial-originated enzyme phospholipase-D.

Preferably, the step of processing is performed in the presence of a buffer having a pH in the range of about 4.5-8.0.

Most preferably, the buffer includes a carboxylic acid with a chain length of C2-C8 having a final concentration in the range of about 0.01M to 0.3M in the pH-buffered aqueous solution.

Preferably, the step of processing is performed in the presence of a calcium salt.

Preferably, the step of processing is performed at a temperature in the range of about 25-60° C.

Preferably, a molar ratio of serine to phosphatides, up to a maximum molar ratio of 20:1, is adjusted to produce the complex.

Preferably, the complex has a product yield of at least about 3% (w/w) phosphatidic acid and at least about 20% (w/w) phosphatidylserine out of the total phospholipid content of the complex.

Preferably, the complex has a product yield above about 10% (w/w) phosphatidic acid and at least about 20% (w/w) phosphatidylserine out of the total phospholipid content of the complex.

Preferably, the complex has a product yield of about 20-70% (w/w) phosphatidic acid and at least about 20% (w/w) phosphatidylserine out of the total phospholipid content of the complex.

Preferably, the phospholipase-D is bound to, the water-insoluble surfactant-matrix material or free in the pH-buffered aqueous solution.

According to the present invention, there is provided for the first time a phosphatide complex, or salt thereof, produced according to the process above.

These and further embodiments will be apparent from the detailed description and examples that follow.

DESCRIPTION OF THE PREFERRED EMBODIMENTS

The present invention relates to processes for the preparation of phosphatides and salts thereof. The principles and operation for preparing phosphatides, according to the present invention, may be better understood with reference to the accompanying description. Exemplary embodiments of the present invention are detailed below in the following three examples of the synthetic processes. It is noted that in the examples that follow, the stationary surfactant matrices used can be generalized to a variety of materials of their respective type.

Example 1

Using soybean lecithin as the raw material, phosphatidyl-L-serine and phosphatidic acid were produced simultaneously by the following process.

50 gr. of a weakly-acidic cation exchanger (Amberlite IRC-50 resin; Sigma-Aldrich Fluka) were placed in a 500-ml. vial, and reacted with 100 gr. of thionylchloride for 12 hrs. at room temperature. The liquid was then decanted, and the residue was treated with excess dodecylamine (150 gr.) for another 12 hrs. at 4° C. The liquid was then decanted, and the residue was washed 4 times with water and dried under reduced pressure to produce the surfactant-matrix material. 50 gr. of soybean lecithin (Epikuron™ 130P powder; Cargill Europe BVBA), 75 gr. amino acid L-serine, 4 gr. calcium chloride, and 150 ml. buffered water (0.1M hexanoic acid, pH-5.0) were added to the surfactant-matrix material in the abovementioned vial, stirred vigorously, and heated to 45° C. for 30 min.

500 U phospholipase-D from cabbage (P 8398 phospholipase-D; Sigma) was added to the mixture for reaction for 1.5 hrs. under stirring with a stirrer at 45° C. In order to inactive the enzyme in the reaction solution, the vial containing the reaction solution was immersed in hot water. Subsequently, the reaction solution was cooled in ice. In order to extract the phospholipids, 75 ml. of distilled water were added to the mixture which was then stirred for 30 min. The solution was then centrifuged for 30 min., separating into two layers. The lower layer was discarded. The remaining upper layer was then dried under reduced pressure. The final composition of phosphatides was determined by HPTLC: PA 21.6%, PS 12.3%, PC 5.3%, and PE 6.8%.

In a second preparation using soybean lecithin as the raw material, phosphatidic acid and phosphatidyl-L-serine were produced simultaneously by the same process as in the first preparation of Example 1 above without the stationary surfactant. The final composition of the phospholipids was determined by HPTLC; PA 15.1%, PS 8.1%, PC 14.1%, and PE 8.6%.

Example 2

Using soybean lecithin as the raw material, phosphatidyl-L-serine was produced by the following process:

50 gr. of a weakly-acidic cation exchanger (Amberlite IRC-50 resin; Sigma-Aldrich Fluka) were placed in a 500-ml vial, and reacted with 100 gr. of thionylchloride for 12 hrs. at room temperature. The liquid was then decanted, and the residue was treated with excess dodecylamine (150 gr.) for another 12 hrs. at 4° C. The liquid was then decanted, and the residue was washed 4 times with water and dried under reduced pressure to produce the surfactant-matrix material. 50 gr. of soybean lecithin (Epikuron™ 130P powder; Cargill Europe BVBA), 75 gr. amino acid L-serine, 4 gr. calcium chloride, and 150 ml. buffered water (0.1M hexanoic acid, pH 5.0) were added to the surfactant-matrix material in the abovementioned vial, stirred vigorously, and heated to 45° C. for 30 min.

500 U phospholipase-D from *Streptomyces* sp. (Sigma-Aldrich P4912) were added to the mixture for reaction for 1.5 hrs. under stirring with a stirrer at 45° C. In order to inactive the enzyme in the reaction solution, the vial containing the reaction solution was immersed in hot water. Subsequently, the reaction solution was cooled in ice. In order to extract the phospholipids, 75 ml. of distilled water were added to the mixture which was then stirred for 30 min. The solution was then centrifuged for 30 min., separating into two layers. The lower layer was discarded. The remaining upper layer was then dried under reduced pressure. The final composition of phosphatides was determined by HPTLC: PS 27.3%, PA 6.6%, PC 4.3%, PE 5.3%.

In a second preparation using soybean lecithin as the raw material, phosphatidyl-L-serine was produced by the same process as in the first preparation of Example 2 above without the stationary surfactant. The final composition of the phospholipids was determined by HPTLC: PS 18.5%, PA 4.3%, PC 13.2%, and PE 7.5%.

Example 3

Using egg yolk lecithin as the raw material, phosphatidyl-L-serine and phosphatidic acid were produced simultaneously by the following process.

50 gr. of a weakly-acidic cation exchanger (Amberlite IRC-50 resin; Sigma-Aldrich Fluka) were placed in a 500-ml. vial, and reacted with 100 gr. of thionylchloride for 12 hrs. at room temperature. The liquid was then decanted, and the residue was treated with excess dodecylamine (150 gr.) for another 12 hrs. at 4° C. The liquid was then decanted, and the residue was washed 4 times with water and dried under reduced pressure to produce the surfactant-matrix material. 50 gr. of egg yolk lecithin (DS-PL95E; Doosan Corp. Venture BG Biotech BU, Korea), 75 gr. amino acid L-serine, 4 gr. calcium chloride, and 150 ml. buffered water (0.1M hexanoic acid, pH 5.0) were added to the surfactant-matrix material in the abovementioned vial, stirred vigorously, and heated to 45° C. for 30 min.

250 U phospholipase-D from *Streptomyces* sp. (Sigma-Aldrich P4912) and 250 U phospholipase-D from cabbage (P 8398 phospholipase-D; Sigma) were added to the mixture for reaction for 5.5 hrs. under stirring with a stirrer at 45° C.

In order to inactive the enzyme in the reaction solution, the vial containing the reaction solution was immersed in hot water. Subsequently, the reaction solution was cooled in ice. In order to extract the phospholipids, 75 ml. of distilled water were added to the mixture which was then stirred for 30 min. The solution was then centrifuged for 30 min., separating into two layers. The lower layer was discarded. The remaining upper layer was then dried under reduced pressure. The final composition of phosphatides was determined by HPTLC. PA 42.6%, PS 43.3%, PC 3.3%, and PE 2.2%.

In a second preparation using egg yolk lecithin as the raw material, phosphatidic acid and phosphatidyl-L-serine were produced simultaneously by the same process as in the first preparation of Example 3 above without the stationary surfactant. The final composition of the phospholipids was determined by HPTLC: PA 35.3%, PS 37.6%, PC 12.2%, and PE 4.2%.

While the invention has been described with respect to a limited number of embodiments, it will be appreciated that many variations, modifications, and other applications of the invention may be made.

What is claimed is:

1. A process for the preparation of phosphatides, or the salts thereof, the process comprising the steps of:
    (a) using at least one raw material lecithin as a substrate and a water-insoluble surfactant-matrix material having a particulate size greater than about 0.01 mm; and
    (b) enzymatically processing said at least one raw material lecithin with said water-insoluble surfactant-matrix material, phospholipase-D, racemic or enantiomerically-pure serine, amino acid, and/or a water-soluble, surfactant-forming amine and salts in a pH-buffered aqueous solution, wherein said step of processing is performed in a single-phase reaction environment, to produce phosphatides, or the salts thereof, having a structural fatty-acid chain derived from said at least one raw material lecithin.

2. The process of claim 1, wherein:
    (i) said at least one raw material lecithin is selected from the group consisting of: a vegetal lecithin and a non-vegetal lecithin;
    (ii) said vegetal lecithin is selected from the group consisting of: soybean lecithin, sunflower lecithin, and rapeseed lecithin;
    (iii) said non-vegetal lecithin is selected from the group consisting of: milk phospholipids, egg yolk lecithin, and fish lecithin;
    (iv) said water-insoluble surfactant-matrix material is selected from the group consisting of: a water-insoluble organic surfactant-matrix material and a water-insoluble inorganic surfactant-matrix material; and (v) said phospholipase-D is selected from the group consisting of: vegetal phospholipase-D, bacterial-originated enzyme phospholipase-D, a combination of vegetal phospholipase-D and bacterial-originated enzyme phospholipase-D.

3. The process of claim 1, wherein said step of processing is performed in the presence of a buffer having a pH in the range of about 4.5-8.0.

4. The process of claim 3, wherein said buffer includes a carboxylic acid with a chain length of C2-C8 having a final concentration in the range of about 0.01M to 0.3M in said pH-buffered aqueous solution.

5. The process of claim 1, wherein said step of processing is performed in the presence of a calcium salt.

6. The process of claim 1, wherein said step of processing is performed at a temperature in the range of about 25-60° C.

7. The process of claim 1, wherein said phospholipase-D is bound to said water-insoluble surfactant-matrix material or free in said pH-buffered aqueous solution.

8. A process for the simultaneous preparation of a complex of phosphatides including phosphatidic acid and phosphatidylserine, or the salts thereof, the process comprising the steps of:
(a) using at least one raw material lecithin as a substrate and a water-insoluble surfactant-matrix material having a particulate size greater than about 0.01 mm; and
(b) enzymatically processing said at least one raw material lecithin with said water-insoluble surfactant-matrix material, phospholipase-D, racemic or enantiomerically-pure serine, amino acid, and/or a water-soluble, surfactant-forming amine and salts in a pH-buffered aqueous solution, wherein said step of processing is performed in a single-phase reaction environment, to produce the complex of phosphatides including phosphatidic acid and phosphatidylserine, or the salts thereof, having, having a structural fatty-acid chain derived from said at least one raw material lecithin.

9. The process of claim 8, wherein:
(i) said at least one raw material lecithin is selected from the group consisting of: a vegetal lecithin and a non-vegetal lecithin;
(ii) said vegetal lecithin is selected from the group consisting of: soybean lecithin, sunflower lecithin, and rapeseed lecithin;
(iii) said non-vegetal lecithin is selected from the group consisting of: milk phospholipids, egg yolk lecithin, and fish lecithin;
(iv) said water-insoluble surfactant-matrix material is selected from the group consisting of: a water-insoluble organic surfactant-matrix material and a water-insoluble inorganic surfactant-matrix material; and
(v) said phospholipase-D is selected from the group consisting of: vegetal phospholipase-D, bacterial-originated enzyme phospholipase-D, a combination of vegetal phospholipase-D and bacterial-originated enzyme phospholipase-D.

10. The process of claim 8, wherein said step of processing is performed in the presence of a buffer having a pH in the range of about 4.5-8.0.

11. The process of claim 10, wherein said buffer includes a carboxylic acid with a chain length of C2-C8 having a final concentration in the range of about 0.01M to 0.3M in said pH-buffered aqueous solution.

12. The process of claim 8, wherein said step of processing is performed in the presence of a calcium salt.

13. The process of claim 8, wherein said step of processing is performed at a temperature in the range of about 25-60° C.

14. The process of claim 8, wherein a molar ratio of serine to phosphatides, up to a maximum molar ratio of 20:1, is adjusted to produce the complex.

15. The process of claim 8, wherein the complex has a product yield of at least about 3% (w/w) phosphatidic acid and at least about 20% (w/w) phosphatidylserine out of the total phospholipid content of the complex.

16. The process of claim 8, wherein the complex has a product yield above about 10% (w/w) phosphatidic acid and at least about 20% (w/w) phosphatidylserine out of the total phospholipid content of the complex.

17. The process of claim 8, wherein the complex has a product yield of about 20-70% (w/w) phosphatidic acid and at least about 20% (w/w) phosphatidylserine out of the total phospholipid content of the complex.

18. The process of claim 8, wherein said phospholipase-D is bound to said water-insoluble surfactant-matrix material or free in said pH-buffered aqueous solution.

\* \* \* \* \*